(12) United States Patent
Kitagawa et al.

(10) Patent No.: US 10,421,853 B2
(45) Date of Patent: Sep. 24, 2019

(54) PHOTOSENSITIVE GAS GENERATING AGENT AND PHOTOCURABLE COMPOSITION

(71) Applicant: CANON KABUSHIKI KAISHA, Tokyo (JP)

(72) Inventors: Kenji Kitagawa, Tokyo (JP); Toshiki Ito, Kawasaki (JP)

(73) Assignee: CANON KABUSHIKI KAISHA, Tokyo (JP)

(*) Notice: Subject to any disclaimer, the term of this patent is extended or adjusted under 35 U.S.C. 154(b) by 601 days.

(21) Appl. No.: 14/766,004

(22) PCT Filed: Mar. 4, 2014

(86) PCT No.: PCT/JP2014/056087
§ 371 (c)(1),
(2) Date: Aug. 5, 2015

(87) PCT Pub. No.: WO2014/136977
PCT Pub. Date: Sep. 12, 2014

(65) Prior Publication Data
US 2015/0368433 A1    Dec. 24, 2015

(30) Foreign Application Priority Data
Mar. 5, 2013    (JP) .................... 2013-043356
Dec. 27, 2013   (JP) .................... 2013-272409

(51) Int. Cl.
*C08K 5/435* (2006.01)
*C07C 311/17* (2006.01)
(Continued)

(52) U.S. Cl.
CPC .......... *C08K 5/435* (2013.01); *B29C 35/0805* (2013.01); *B29C 59/005* (2013.01);
(Continued)

(58) Field of Classification Search
None
See application file for complete search history.

(56) References Cited

U.S. PATENT DOCUMENTS 3,993,638 A * 11/1976 Fleckenstein ........... C09B 29/00
534/573
6,352,811 B1 * 3/2002 Patel .................... B41C 1/1016
101/467
(Continued)

FOREIGN PATENT DOCUMENTS

JP    2006-287012 A    10/2006
JP    2010-107957 A     5/2010
(Continued)

OTHER PUBLICATIONS

First Office Action in Chinese Application No. 201480012262.8 (dated Jan. 4, 2017).
(Continued)

*Primary Examiner* — Scott R. Walshon
*Assistant Examiner* — Elaine M Vazquez
(74) *Attorney, Agent, or Firm* — Venable LLP

(57) ABSTRACT

A photocurable composition excellent in the effect of reducing the mold releasing force even in a small amount of light exposure, and a photosensitive gas generating agent contained in the photocurable composition are provided.

The photosensitive gas generating agent is a compound having a photostimulation responsive gas generating group to generate a gas by photostimulation, a perfluoroalkyl group and a polyalkyleneoxy group to link the photostimulation responsive gas generating group and the perfluoroalkyl group. The photocurable composition contains the photosensitive gas generating agent.

13 Claims, 1 Drawing Sheet

(51) Int. Cl.
- *C08F 2/48* (2006.01)
- *G03F 7/00* (2006.01)
- *H01L 21/02* (2006.01)
- *H01L 21/027* (2006.01)
- *B29C 35/08* (2006.01)
- *B29C 59/00* (2006.01)
- *B29C 59/02* (2006.01)
- *B29D 11/00* (2006.01)
- *C07C 311/44* (2006.01)
- *G03F 7/004* (2006.01)
- *B29K 33/00* (2006.01)
- *B29L 31/34* (2006.01)

(52) U.S. Cl.
CPC ...... *B29C 59/026* (2013.01); *B29D 11/00865* (2013.01); *C07C 311/17* (2013.01); *C07C 311/44* (2013.01); *C08F 2/48* (2013.01); *G03F 7/0002* (2013.01); *G03F 7/0046* (2013.01); *H01L 21/0274* (2013.01); *H01L 21/02118* (2013.01); *B29K 2033/12* (2013.01); *B29L 2031/3425* (2013.01); *Y10T 428/24612* (2015.01)

(56) References Cited

U.S. PATENT DOCUMENTS

| | | |
|---|---|---|
| 2015/0050426 A1 | 2/2015 | Ito et al. |
| 2015/0075855 A1 | 3/2015 | Ito et al. |
| 2015/0210790 A1 | 7/2015 | Ito et al. |

FOREIGN PATENT DOCUMENTS

| | | |
|---|---|---|
| JP | 2010-262980 A | 11/2010 |
| JP | 2011-071299 A | 4/2011 |
| JP | 2012-220855 A | 11/2012 |
| KR | 10-2010-0037547 | 4/2010 |
| WO | 2010/005032 A1 | 1/2010 |

OTHER PUBLICATIONS

Notice of Preliminary Rejection in Korean Application No. 10-2015-7026277 (dated Jul. 12, 2016).

Extended European Search Report in European Application No. 14761040.6 (dated Aug. 23, 2016).

Office Action in Taiwanese Application No. 103107427 (dated May 5, 2015).

Matthew Colburn et al., "Step and Flash Imprint Lithography: A New Approach to High-Resolution Patterning," 3676 SPIE 379-389 (Jun. 1999).

* cited by examiner

PHOTOSENSITIVE GAS GENERATING AGENT AND PHOTOCURABLE COMPOSITION

TECHNICAL FIELD

The present invention relates to a photosensitive gas generating agent, and a photocurable composition containing the photosensitive gas generating agent.

BACKGROUND ART

A photo-nanoimprinting method is, for example, as described in Non Patent Literature 1, one method for fabricating a resist film having a predetermined pattern shape on a substrate such as a base material to be processed, and has the following production process of (a) to (d):
(a) a disposing step of disposing a resist (photocurable composition);
(b) a mold contact step of bringing the photocurable composition into contact with a mold on whose surface a fine protruding and recessed pattern is formed;
(c) a light irradiation step of irradiating the photocurable composition with light; and
(d) after the light irradiation step, a mold releasing step of separating the photocurable composition from the mold.

Here, the pattern shape of the resist film fabricated through the above production process of (a) to (d) is formed by transferring the protrusions and recesses of the mold to the resist film disposed on a substrate.

Here, in utilization of the photo-nanoimprinting method, reduction of a force needed to separate (mold release) the mold from a cured resist in the mold releasing step (step (d)), that is, a mold releasing force, has become an important problem. This is because if the mold releasing force is large, problems arise such as causing defects in the pattern and reducing the positioning accuracy due to lifting of the substrate from a stage.

One method for reducing the mold releasing force is a method of incorporating a photosensitive gas generating agent in a photocurable composition. This method is a method in which a gas generated when the photocurable composition is irradiated with light is caused to intervene between a mold and the photocurable composition to thereby reduce the mold releasing force by utilization of a pressure of the gas.

As photosensitive gas generating agents for nanoimprint lithography, for example, azo compounds, diazonium compounds, azide compounds, naphthoquinone compounds, sulfohydrazide compounds and hydrazo compounds, which are disclosed in Patent Literature 1, are known.

CITATION LIST

Patent Literature

PTL 1: Japanese Patent Application Laid-Open No. 2010-262980

Non Patent Literature

NPL 1: SPIE, vol. 3676, p. 379

SUMMARY OF INVENTION

Technical Problem

However, the case where a pattern is formed by the photo-nanoimprinting method using a photocurable composition (photocurable composition containing a photosensitive gas generating agent) described in Patent Literature 1 has a problem described below. That is, in the case of a small amount of light exposure, the photocurable composition described in Patent Literature 1 poses such a problem that the mold releasing force generated between a mold and a cured resist when the mold is separated (mold released) from the cured resist becomes large and defects in the pattern and distortion in a substrate are liable to be caused.

The present invention has been achieved to solve the above-mentioned problem, and an object of the present invention is to provide a photocurable composition excellent in the effect of reducing the mold releasing force even in a small amount of light exposure, and a photosensitive gas generating agent contained in the photocurable composition.

Solution to Problem

The photosensitive gas generating agent according to the present invention is a compound having a photostimulation responsive gas generating group to generate a gas by photostimulation, a perfluoroalkyl group, and a polyalkyleneoxy group to link the photostimulation responsive gas generating group and the perfluoroalkyl group.

Advantageous Effects of Invention

The present invention can provide a photocurable composition excellent in the effect of reducing the mold releasing force even in a small amount of light exposure, and a photosensitive gas generating agent contained in the photocurable composition.

Further features of the present invention will become apparent from the following description of exemplary embodiments with reference to the attached drawings.

BRIEF DESCRIPTION OF DRAWINGS

FIG. 1B1 is a cross-sectional schematic diagram illustrating an example of the embodiment in the production method of a film according to the present invention.

FIG. 1B2 is a cross-sectional schematic diagram illustrating an example of the embodiment in the production method of a film according to the present invention.

DESCRIPTION OF EMBODIMENTS

Figure 1A:
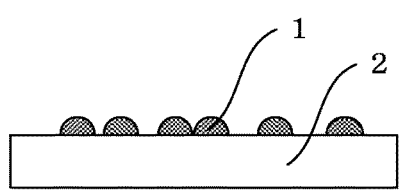
FIG. 1A is a cross-sectional schematic diagram illustrating an example of an embodiment in the production method of a film according to the present invention.
Figure 1A:
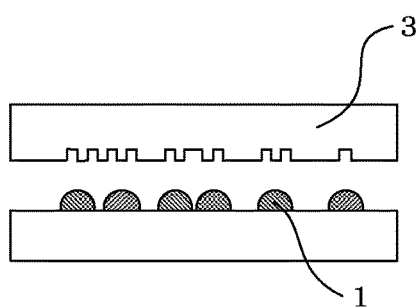
Figure 1A:
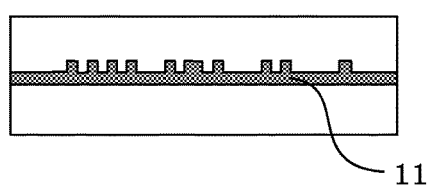

Hereinafter, embodiments according to the present invention will be described in detail. However, the present invention is not limited to the embodiments described below. That is, without departing from the gist of the present invention, suitable changes and modification may naturally be made on the following embodiments, based on the usual knowledge of those skilled in the art.

(1) The Photosensitive Gas Generating Agent

First, the photosensitive gas generating agent according to the present invention will be described.

The photosensitive gas generating agent according to the present invention is a compound having substituents represented by the following (1A) to (1C):

(1A) a photostimulation responsive gas generating group to generate a gas by photostimulation;

(1B) a perfluoroalkyl group; and (1C) a polyalkyleneoxy group to link the photostimulation responsive gas generating group and the perfluoroalkyl group.

Here, at least one substituent of each of the above substituents of (1A) to (1C) is contained in a compound to become the photosensitive gas generating agent. That is, the numbers of the above substituents of (1A) to (1C) in the compound may be each one or more, and are not limited. Hereinafter, the above substituents of (1A) to (1C) will be described specifically.

(1A) A Photostimulation Responsive Gas Generating Group

A photostimulation responsive gas generating group is a substituent having a functional group to absorb light in a specific wavelength such as ultraviolet rays to thereby cause a chemical reaction (photodecomposition), and to generate a gas as a result of the chemical reaction (photodecomposition). The gas generated by the photodecomposition specifically includes carbon dioxide, carbon monoxide, nitrogen, oxygen and hydrogen, but carbon dioxide or nitrogen is preferable.

A photostimulation responsive carbon dioxide gas generating group to generate carbon dioxide (or carbon monoxide) by photodecomposition includes a nitrobenzyloxycarbonyl oxyimino group and a benzoinoxycarbonyl oxyimino group.

A photostimulation responsive gas generating group to generate nitrogen by photodecomposition includes an azo group, a diazo group, an azide group, a sulfonohydrazide group and a hydrazo group.

Among these substituents, photostimulation responsive nitrogen gas generating groups are preferable, and among photostimulation responsive nitrogen gas generating groups, a diazo group is preferable, from the viewpoint of being excellent in responsiveness to photostimulation.

Examples of substituents having a diazo group include diazonaphthoquinonesulfonyl groups (2-diazo-1,2-naphthoquinone-5-sulfonyl group, 2-diazo-1,2-naphthoquinone-4-sulfonyl group and the like), and substituents including bissulfonyldiazomethane derivatives described in Patent Literature 1. Among these organic groups, a diazonaphthoquinonesulfonyl group is preferable from the viewpoint of being excellent in the effect of reducing the mold releasing force when used in nanoimprint lithography.

(1B) A Perfluoroalkyl Group

A perfluoroalkyl group is an alkyl group containing a carbon atom and a fluorine atom, but may contain a certain number of hydrogen atoms in the substituent under the condition of not exceeding the number of fluorine atoms. However, the perfluoroalkyl group contains no other atoms than a carbon atom, a fluorine atom and a hydrogen atom. In the case where a perfluoroalkyl group contains a hydrogen atom, the number of hydrogen atoms is preferably equal to or less than half the number of fluorine atoms, and more preferably equal to or less than one third of the number of fluorine atoms. By making the number of hydrogen atoms in this range, the hydrophobicity of the perfluoroalkyl group is likely to act effectively.

The perfluoroalkyl group specifically includes a trifluoromethyl group ($-CF_3$), a perfluoroethyl group ($-CF_2CF_3$), a perfluoropropyl group ($-C_3F_7$), a perfluorobutyl group ($-C_4F_9$), a perfluoropentyl group ($-C_5F_{11}$), a perfluorohexyl group ($-C_6F_{13}$), a 1H,1H-perfluoroheptyl group ($C_6F_{13}-CH_2-$), a 1H,1H,2H,2H-perfluorooctyl group ($C_6F_{13}-CH_2CH_2-$) and a 1H, 1H, 2H, 2H, 3H, 3H-perfluorononyl group ($C_6F_{13}-C_3H_6-$). Among these perfluoroalkyl groups, a perfluorohexyl group, a 1H,1H-perfluoroheptyl group, a 1H,1H,2H,2H-perfluorooctyl group and a 1H,1H,2H,2H,3H,3H-perfluorononyl group are preferable, and a perfluorohexyl group, a 1H,1H-perfluoroheptyl group and a 1H,1H,2H,2H-perfluorooctyl group are more preferable, from the viewpoint of being high in hydrophobicity.

If a compound to become a photosensitive gas generating agent contains a perfluoroalkyl group being a hydrophobic substituent, the photosensitive gas generating agent comes to be easily present at a gas-liquid interface. Therefore, a gas generated from a photostimulation responsive gas generating group can be generated intensively at the gas-liquid interface.

That is, if a photocurable composition containing a photosensitive gas generating agent is applied in a gas atmosphere of air, nitrogen, helium or the like, the photosensitive gas generating agent is distributed unevenly on the surface of the photocurable composition. Therefore, if the photosensitive gas generating agent according to the present invention is incorporated in a photocurable composition and the photocurable composition is photocured, it is likely that whereas a gas is generated from the surface of the photocurable composition, bubbling is hardly caused in the interior of the photocurable composition.

(1C) A Polyalkyleneoxy Group

A polyalkyleneoxy group specifically includes a polyethyleneoxy group, a polypropyleneoxy group, polytrimethyleneoxy group and a polytetramethyleneoxy group. These may be mixtures.

Here, if a compound contains a polyalkyleneoxy group, physical properties such as the hydrophilicity of the photosensitive gas generating agent and the solubility thereof to a specific solvent (including a polymerizable compound (A) described later and an organic solvent) can be controlled. Since the use of, for example, a polyethyleneoxy group improves the hydrophilicity, the affinity for a hydrophilic surface (for example, surface of quartz) and the solubility to a high-polarity solvent are likely to be excellent. On the other hand, if a polypropyleneoxy group is used, the solubility to a low-polarity solvent is likely to be excellent.

As described hitherto, a compound used as the photosensitive gas generating agent according to the present invention contains, at least, a photostimulation responsive gas generating group, a perfluoroalkyl group and a polyalkyleneoxy group. Here, the compound used as the photosensitive gas generating agent according to the present invention not only contains these three substituents, but may further contain other functional groups (an alkylene group, an alkyl group, an amino group, a carboxyl group and the like).

Then, compounds preferable as a photosensitive gas generating agent will be described. Among compounds used as the photosensitive gas generating agent according to the present invention, a compound represented by the following general formula (1) is preferable from the viewpoint of the production cost, the ease of handling and the like.

$$R_{G1}-X_A-(O-R_1)_n-O-R_f \quad (1)$$

In the formula (1), $R_{G1}$ represents a photostimulation responsive gas generating group. The photostimulation responsive gas generating group represented by $R_{G1}$ includes a photostimulation responsive carbon dioxide gas generating group and a photostimulation responsive nitrogen gas generating group which are described above, but is not especially limited. Specific examples of $R_{G1}$ include substituents represented by the following formulae (P), (Q), (R), (S) and (T).

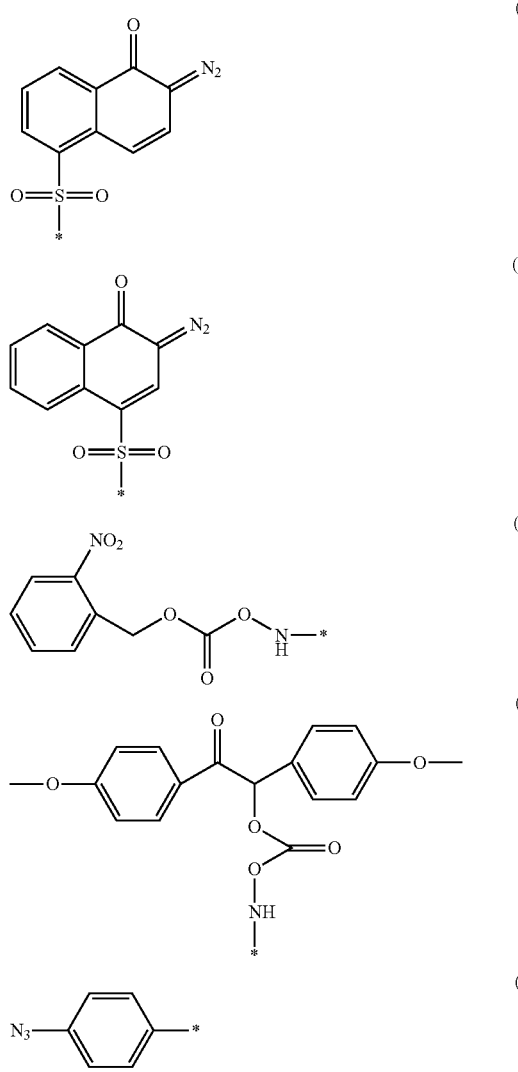

In the formulae (P) to (T), * represents a bond to bond with $X_A$.

The substituent of the formula (P) is a 2-diazo-1,2-naphthoquinone-5-sulfonyl group to generate nitrogen gas by photostimulation; the substituent of the formula (Q) is a 2-diazo-1,2-naphthoquinone-4-sulfonyl group to generate nitrogen gas by photostimulation; the substituent of the formula (R) is a nitrobenzyloxycarbonyl oxyimino group to generate carbon dioxide gas by photostimulation; the substituent of the formula (S) is a benzoinoxycarbonyl oxyimino group to generate carbon dioxide gas by photostimulation; and the substituent of the formula (T) is an azide phenylene group to generate nitrogen gas by photostimulation.

In the formula (1), $X_A$ represents a divalent substituent to become a linking group. The linking group (divalent substituent) represented by $X_A$ specifically includes an oxygen atom (oxy group), a sulfur atom (thio group), an alkylene group, a phenylene group, a naphthylene group, a carbonyl group, a sulfonyl group, an imino group (—NH—), an alkylimino group (—NR— (R represents an alkyl group)), an amide group and a urethane group. The linking group also includes substituents formed by selecting two or more of these divalent substituents, for example, an oxycarbonyl group (ester bond) and an ethyliminoethyl group (—N(—C$_2$H$_5$)—C$_2$H$_4$—)).

In the formula (1), O represents an oxygen atom.

In the formula (1), $R_1$ represents an alkylene group having 2 to 4 carbon atoms. The alkylene group represented by $R_1$ specifically includes an ethylene group, a propylene group, a trimethylene group and a tetramethylene group.

In the formula (1), n represents an integer of 2 to 30. Setting n in this range allows a low production cost and easy handling. By contrast, n larger than 30 gives a high viscosity, and is likely to make the handling difficult. The case where n is 1 is likely to bring about a high production cost.

In the formula (1), $R_f$ represents a monovalent perfluoroalkyl group. The perfluoroalkyl group represented by $R_f$ specifically includes a trifluoromethyl group (—CF$_3$), a perfluoroethyl group (—CF$_2$CF$_3$), a perfluoropropyl group (—C$_3$F$_7$), a perfluorobutyl group (—C$_4$F$_9$), a perfluoropentyl group (—C$_5$F$_{11}$), a perfluorohexyl group (—C$_6$F$_{13}$), a 1H,1H-perfluoroheptyl group (C$_6$F$_{13}$—CH$_2$—), a 1H,1H,2H,2H-perfluorooctyl group (C$_6$F$_{13}$—CH$_2$CH$_2$—) and a 1H,1H,2H, 2H, 3H, 3H-perfluorononyl group (C$_6$F$_{13}$—C$_3$H$_6$—). Among these perfluoroalkyl groups, a perfluorohexyl group, a 1H,1H-perfluoroheptyl group, a 1H,1H,2H,2H-perfluorooctyl group and a 1H,1H,2H,2H,3H,3H-perfluorononyl group are preferable, from the viewpoint of being high in hydrophobicity. A perfluorohexyl group, a 1H,1H-perfluoroheptyl group and a 1H,1H,2H,2H-perfluorooctyl group are more preferable, from the viewpoint of easily unevenly distributing a photosensitive gas generating agent at the gas-liquid interface.

Among compounds represented by the formula (1), a compound represented by the following general formula (2) is preferable. A compound of the following general formula (2) among the compounds of the formula (1), because being better in the effect of reducing the mold releasing force when used for nanoimprint lithography, is more preferable as the photosensitive gas generating agent according to the present invention.

$$R_{G2}-\underset{R_2}{N}-X_B-(O-R_1)_n-O-R_f \quad (2)$$

In the formula (2), $R_{G2}$ represents a diazonaphthoquinonesulfonyl group. The diazonaphthoquinonesulfonyl group represented by $R_{G2}$ specifically includes substituents represented by the following formulae (P') and (Q').

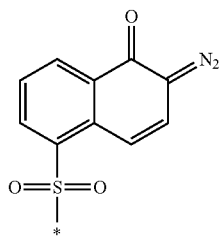

(P')

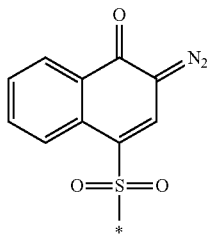

(Q')

In the formulae (P') and (Q'), * represents a bond to bond with N.

In the formula (2), N represents a nitrogen atom, and O represents an oxygen atom. Here, a nitrogen atom (N atom) to bond with $R_{G2}$ plays a role of improving the preservation stability of the compound itself.

In the formula (2), $X_B$ represents an alkylene group having 1 to 4 carbon atoms, and preferably an alkylene group having 2 to 4 carbon atoms. If the number of carbon atoms is in the range of 1 to 4, in use for nanoimprint lithography, the mold releasing force is low, which is therefore preferable. Further if the number of carbon atoms is 2 to 4, since compounds of the formula (2) can be synthesized from easily available materials such as polyalkylene oxide adducts of perfluoroalkyl alcohols, alkylamines and diazonaphthoquinone chloride, the cost reduction can be achieved. The alkylene group represented by $X_B$ specifically includes a methylene group, an ethylene group, a propylene group (—CH(CH$_3$)CH$_2$—), a trimethylene group and a tetramethylene group.

In the formula (2), $R_1$ represents an alkylene group having 2 to 4 carbon atoms. Specific examples of the alkylene group represented by $R_1$ are the same as the specific examples of $R_1$ in the formula (1). $R_1$ is preferably an ethylene group or a propylene group, and especially preferably an ethylene group. By allocating an ethylene group or a propylene group as $R_1$, when the photosensitive gas generating agent is brought into contact with a polar surface such as a quartz surface after the photosensitive gas generating agent is unevenly distributed at the gas-liquid interface, the photosensitive gas generating agent is easily unevenly distributed on the polar surface because the polyalkyleneoxy group is a substituent having a high affinity for the polar surface. That is, by allocating an ethylene group or a propylene group as $R_1$ to make good the affinity of the polyalkyleneoxy group for a medium having a polarity, the photosensitive gas generating agent can be unevenly distributed in a best region in a film production process described later.

In the formula (2), n represents an integer of 2 to 30. Setting n in this range as in the compounds of the formula (1) allows a low production cost and easy handling. n is preferably an integer of 3 to 25, and especially preferably an integer of 4 to 20. By setting n in such a range, in the case where a photocurable composition containing the photosensitive gas generating agent according to the present invention is used for nanoimprint lithography, the photocurable composition can be provided which is easily mold-releasable even in a small amount of light exposure. By setting n in such a range, the surface of a quartz mask is likely to be hardly contaminated.

In the formula (2), $R_f$ represents a monovalent perfluoroalkyl group. Specific examples of the perfluoroalkyl group represented by $R_f$ are the same as the specific examples of $R_f$ in the formula (1).

In the formula (2), $R_2$ represents an alkyl group having 1 to 6 carbon atoms. By allocating an alkyl group having 1 to 6 carbon atoms as $R_2$, since the extraction operation and the like become easy when a compound to become a photosensitive gas generating agent is synthesized, the effect of improving the yield is attained.

A compound of the general formula (2), in the case of being used for nanoimprint lithography, has an excellent effect of reducing the mold releasing force in a small amount of light exposure. Therefore, the compound of the general formula (2) is especially preferable as a photosensitive gas generating agent for nanoimprint lithography.

(2) The Photocurable Composition

Then, the photocurable composition according to the present invention will be described. The photocurable composition according to the present invention has, at least, a component (A) to a component (C) described below.

(A) A polymerizable compound
(B) A photopolymerization initiator
(C) A photosensitive gas generating agent In the present invention, a photosensitive gas generating agent being a component (C) is the photosensitive gas generating agent according to the present invention. In the photocurable composition according to the present invention, the content of a photosensitive gas generating agent being a component (C) is not especially limited, but preferably 0.1 wt % to 50 wt %, more preferably 1 wt % to 30 wt %, and especially preferably 5 wt % to 20 wt %, based on the weight of a polymerizable compound (component (A)) contained in the photocurable composition. If the relative content of a photosensitive gas generating agent (component (C)) based on the weight of a polymerizable compound is made to be less than 0.1 wt %, the advantageous effects of the present invention may not possibly be attained sufficiently. If the content of a photosensitive gas generating agent (component (C)) exceeds 50 wt %, the mechanical strength of an obtained film which the film is expected to have may not be sufficiently secured, which may cause pattern defects.

The ratio (C/B) of a weight of a photosensitive gas generating agent (component (C)) to a weight of a photopolymerization initiator (component (B)) is preferably 1 to 1,000, more preferably 1.5 to 100, and especially preferably 2 to 10. By setting the ratio at least in the range of 1 to 1,000, in the case where a photocurable composition is used for nanoimprint lithography, the balance between the curing speed of the photocurable composition and the generation speed of a gas generated from the photocurable composition is excellent. Therefore, if a photocurable composition whose C/B value is set in the range of 1 to 1,000 is used for nanoimprint lithography, bubbling in the interior of a film is hardly caused, and the effect of reducing the mold releasing force in a small amount of light exposure is attained.

The reason therefor is conceivably as follows.

In the case where the C/B value is lower than 1, it is conceivable that since although the curing of a curable composition is fast, the gas generation speed is likely to become low, the amount of light exposure until the effect of reducing the mold releasing force is attained is likely to become large.

By contrast, in the case where the C/B exceeds 1,000, it is conceivable that since although the gas generation speed is fast, the curing of a curable composition is likely to become slow, a gas is generated in the interior of the curable composition before the curable composition is fully cured, and bubbling easily occurs.

Then, components (A) and (B) contained in the photocurable composition according to the present invention will be described.

(2-1) A Polymerizable Compound (Component (A))

Examples of a polymerizable compound include radically polymerizable compounds and cationically polymerizable compounds.

The radically polymerizable compound can be a compound having one or more acryloyl groups or methacryloyl groups. On the other hand, the cationically polymerizable compound can be a compound having one or more vinyl ether groups, epoxy groups or oxetanyl groups. Hereinafter, specific examples of the radically polymerizable compound and the cationically polymerizable compound will be each described.

(2-1-1) A Polymerizable Compound (Component (A))—A Radically Polymerizable Compound Examples of a monofunctional (meth)acrylic compound having one acryloyl or methacryloyl group include, but are not limited to, phenoxyethyl (meth)acrylate, phenoxy-2-methylethyl (meth)acrylate, phenoxyethoxyethyl (meth)acrylate, 3-phenoxy-2-hydroxypropyl (meth)acrylate, 2-phenylphenoxyethyl (meth)acrylate, 4-phenylphenoxyethyl (meth)acrylate, 3-(2-phenylphenyl)-2-hydroxypropyl (meth)acrylate, (meth)acrylate of EO-modified p-cumylphenol, 2-bromophenoxyethyl (meth)acrylate, 2,4-dibromophenoxyethyl (meth)acrylate, 2,4,6-tribromophenoxyethyl (meth)acrylate, EO-modified phenoxy (meth)acrylate, PO-modified phenoxy (meth)acrylate, polyoxyethylene nonylphenyl ether (meth)acrylate, isobornyl (meth)acrylate, 1-adamantyl (meth)acrylate, 2-methyl-2-adamantyl (meth)acrylate, 2-ethyl-2-adamantyl (meth)acrylate, bornyl (meth)acrylate, tricyclodecanyl (meth)acrylate, dicyclopentanyl (meth)acrylate, dicyclopentenyl (meth)acrylate, cyclohexyl (meth)acrylate, 4-butylcyclohexyl (meth)acrylate, acryloyl morpholine, 2-hydroxyethyl (meth)acrylate, 2-hydroxypropyl (meth)acrylate, 2-hydroxybutyl (meth)acrylate, methyl (meth)acrylate, ethyl (meth)acrylate, propyl (meth)acrylate, isopropyl (meth)acrylate, butyl (meth)acrylate, amyl (meth)acrylate, isobutyl (meth)acrylate, t-butyl (meth)acrylate, pentyl (meth)acrylate, isoamyl (meth)acrylate, hexyl (meth)acrylate, heptyl (meth)acrylate, octyl (meth)acrylate, isooctyl (meth)acrylate, 2-ethylhexyl (meth)acrylate, nonyl (meth)acrylate, decyl (meth)acrylate, isodecyl (meth)acrylate, undecyl (meth)acrylate, dodecyl (meth)acrylate, lauryl (meth)acrylate, stearyl (meth)acrylate, isostearyl (meth)acrylate, benzyl (meth)acrylate, tetrahydrofurfuryl (meth)acrylate, butoxy ethyl (meth)acrylate, ethoxy diethylene glycol (meth)acrylate, polyethylene glycol mono(meth)acrylate, polypropylene glycol mono (meth)acrylate, methoxy ethylene glycol (meth)acrylate, ethoxy ethyl (meth)acrylate, methoxy polyethylene glycol (meth)acrylate, methoxy polypropylene glycol (meth)acrylate, diacetone (meth)acrylamide, isobutoxy methyl (meth)acrylamide, N,N-dimethyl (meth)acrylamide, t-octyl (meth) acrylamide, dimethyl amino ethyl (meth)acrylate, diethyl amino ethyl (meth)acrylate, 7-amino-3,7-dimethyloctyl (meth)acrylate, N,N-diethyl (meth)acrylamide and N,N-dimethyl amino propyl (meth)acrylamide.

Commercially available products corresponding to these monofunctional (meth)acrylic compounds include, but are not limited to, Aronix M101, M102, M110, M111, M113, M117, M5700, TO-1317, M120, M150 and M156 (all manufactured by Toagosei Co., Ltd.), MEDOL10, MIBDOL10, CHDOL10, MMDOL30, MEDOL30, MIBDOL30, CHDOL30, LA, IBXA, 2-MTA, HPA, Viscoat #150, #155, #158, #190, #192, #193, #220, #2000, #2100 and #2150 (all manufactured by Osaka Organic Chemical Industry Ltd.), Light acrylate BO-A, EC-A, DMP-A, THF-A, HOP-A, HOA-MPE, HOA-MPL, PO-A, P-200A, NP-4EA and NP-8EA, and Epoxy ester M-600A (all manufactured by Kyoeisha Chemical Co., Ltd.), KAYARAD TC110S, R-564 and R-128H (all manufactured by Nippon Kayaku Co., Ltd.), NK ester AMP-10G and AMP-20G (all manufactured by Shin-Nakamura Chemical Co., Ltd.), FA-511A, 512A and 513A (all manufactured by Hitachi Chemical Co., Ltd.), PHE, CEA, PHE-2, PHE-4, BR-31, BR-31M and BR-32 (all manufactured by Dai-Ichi Kogyo Seiyaku Co., Ltd.), VP (manufactured by BASF SE) and ACMO, DMAA and DMAPAA (all manufactured by Kohjin Holdings Co., Ltd.).

Examples of a polyfunctional (meth)acrylic compound having two or more acryloyl or methacryloyl groups include, but are not limited to, trimethylolpropane di(meth)acrylate, trimethylolpropane tri(meth)acrylate, EO-modified trimethylolpropane tri(meth)acrylate, PO-modified trimethylolpropane tri(meth)acrylate, EO,PO-modified trimethylolpropane tri(meth)acrylate, pentaerythritol tri(meth)acrylate, pentaerythritol tetra(meth)acrylate, ethylene glycol di(meth)acrylate, tetraethylene glycol di(meth)acrylate, polyethylene glycol di(meth)acrylate, polypropylene glycol di(meth)acrylate, 1,4-butanediol di(meth)acrylate, 1,6-hexanediol di(meth)acrylate, neopentyl glycol di(meth)acrylate, tris(2-hydroxyethyl) isocyanurate tri(meth)acrylate, tris (acryloyloxy) isocyanurate, bis(hydroxymethyl) tricyclodecane di(meth)acrylate, dipentaerythritol penta (meth)acrylate, dipentaerythritol hexa(meth)acrylate, EO-modified 2,2-bis(4-((meth)acryloxy)phenyl)propane, PO-modified 2,2-bis(4-((meth)acryloxy)phenyl)propane and EO, PO-modified 2,2-bis(4-((meth)acryloxy)phenyl) propane.

Commercially available products corresponding to these polyfunctional (meth)acrylic compounds include, but are not limited to, Upimer UV SA1002 and SA2007 (both manufactured by Mitsubishi Chemical Corporation), Viscoat #195, #230, #215, #260, #335HP, #295, #300, #360, #700, GPT and 3PA (all manufactured by Osaka Organic Chemical Industry Ltd.), Light acrylate 4EG-A, 9EG-A, NP-A, DCP-A, BP-4EA, BP-4PA, TMP-A, PE-3A, PE-4A and DPE-6A (all manufactured by Kyoeisha Chemical Co., Ltd.), KAYARAD PET-30, TMPTA, R-604, DPHA, DPCA-20, -30, -60 and -120, HX-620, D-310 and D-330 (all manufactured by Nippon Kayaku Co., Ltd.), Aronix M208, M210, M215, M220, M240, M305, M309, M310, M315, M325 and M400 (all manufactured by Toagosei Co., Ltd.) and Ripoxy VR-77, VR-60 and VR-90 (all manufactured by Showa Highpolymer Co., Ltd.).

The radically polymerizable compounds cited hitherto may be used singly or in combinations of two or more. In the above, a (meth)acrylate refers to a concept consisting of an acrylate and a methacrylate corresponding thereto. A (meth) acryloyl group refers to a concept including an acryloyl group and a methacryloyl group corresponding thereto. EO represents ethylene oxide, and an EO-modified compound means a compound having a block structure of an ethylene oxide group. PO represents propylene oxide, and a PO-modified compound means a compound having a block structure of a propylene oxide group.

(2-1-2) A Polymerizable Compound (Component (A))—A Cationically Polymerizable Compound Examples of a compound having one vinyl ether group include, but are not limited to, methyl vinyl ether, ethyl vinyl ether, propyl vinyl ether, n-butyl vinyl ether, t-butyl vinyl ether, 2-ethylhexyl vinyl ether, n-nonyl vinyl ether, lauryl vinyl ether, cyclohexyl vinyl ether, cyclohexyl methyl vinyl ether, 4-methyl cyclohexyl methyl vinyl ether, benzyl vinyl ether, dicyclopentenyl vinyl ether, 2-dicyclopentenoxyethyl vinyl ether, methoxyethyl vinyl ether, ethoxyethyl vinyl ether, butoxyethyl vinyl ether, methoxyethoxyethyl vinyl ether, ethoxyethoxyethyl vinyl ether, methoxypolyethylene glycol vinyl ether, tetrahydrofurfuryl vinyl ether, 2-hydroxyethyl vinyl ether, 2-hydroxypropyl vinyl ether, 4-hydroxybutyl vinyl ether, 4-hydroxymethyl cyclohexylmethyl vinyl ether, diethylene glycol mono vinyl ether, polyethylene glycol vinyl ether, chloroethyl vinyl ether, chlorobutyl vinyl ether, chloroethoxyethyl vinyl ether, phenylethyl vinyl ether and phenoxypolyethylene glycol vinyl ether.

Examples of a compound having two or more vinyl ether groups include, but are not limited to, divinyl ethers such as ethylene glycol divinyl ether, diethylene glycol divinyl ether, polyethylene glycol divinyl ether, propylene glycol divinyl ether, butylene glycol divinyl ether, hexanediol divinyl ether, bisphenol A alkylene oxide divinyl ether and bisphenol F alkylene oxide divinyl ether; and polyfunctional vinyl ethers such as trimethylolethane trivinyl ether, trimethylolpropane trivinyl ether, ditrimethylolpropane tetravinyl ether, glycerin trivinyl ether, pentaerythritol tetravinyl ether, dipentaerythritol pentavinyl ether, dipentaerythritol hexavinyl ether, ethylene oxide-added trimethylolpropane trivinyl ether, propylene oxide-added trimethylolpropane trivinyl ether, ethylene oxide-added ditrimethylolpropane tetravinyl ether, propylene oxide-added ditrimethylolpropane tetravinyl ether, ethylene oxide-added pentaerythritol tetravinyl ether, propylene oxide-added pentaerythritol tetravinyl ether, ethylene oxide-added dipentaerythritol hexavinyl ether and propylene oxide-added dipentaerythritol hexavinyl ether.

Examples of a compound having one epoxy group include, but are not limited to, phenyl glycidyl ether, p-tert-butylphenyl glycidyl ether, butyl glycidyl ether, 2-ethylhexyl glycidyl ether, allyl glycidyl ether, 1,2-butylene oxide, 1,3-butadiene monoxide, 1,2-epoxydodecane, epichlorohydrin, 1,2-epoxydecane, styrene oxide, cyclohexene oxide, 3-methacryloyloxy methylcyclohexene oxide, 3-acryloyloxy methylcyclohexene oxide and 3-vinylcyclohexene oxide.

Examples of a compound having two or more epoxy groups include, but are not limited to, bisphenol A diglycidyl ether, bisphenol F diglycidyl ether, bisphenol S diglycidyl ether, brominated bisphenol A diglycidyl ether, brominated bisphenol F diglycidyl ether, brominated bisphenol S diglycidyl ether, an epoxy novolac resin, hydrogenated bisphenol A diglycidyl ether, hydrogenated bisphenol F diglycidyl ether, hydrogenated bisphenol S diglycidyl ether, 3,4-epoxycyclohexylmethyl-3',4'-epoxycyclohexane carboxylate, 2-(3,4-epoxycyclohexyl-5,5-spiro-3,4-epoxy)cyclohexane-meta-dioxane, bis(3,4-epoxycyclohexylmethyl)adipate, vinyl cyclohexene oxide, 4-vinylepoxycyclohexane, bis(3,4-epoxy-6-methylcyclohexylmethyl)adipate, 3,4-epoxy-6-methylcyclohexyl-3',4'-epoxy-6'-methylcyclohexane carboxylate, methylene bis(3,4-epoxycyclohexane), dicyclopentadiene diepoxide, di(3,4-epoxycyclohexylmethyl) ether of ethylene glycol, ethylene bis(3,4-epoxycyclohexane carboxylate), dioctyl epoxyhexahydrophthalate, di-2-ethylhexyl epoxyhexahydrophthalate, 1,4-butanediol diglycidyl ether, 1,6-hexanediol diglycidyl ether, glycerin triglycidyl ether, trimethylolpropane triglycidyl ether, polyethylene glycol diglycidyl ether, polypropylene glycol diglycidyl ethers, 1,1,3-tetradecadiene dioxide, limonene dioxide, 1,2,7,8-diepoxyoctane and 1,2,5,6-diepoxycyclooctane.

Examples of a compound having one oxetanyl group include, but are not limited to, 3-ethyl-3-hydroxymethyl oxetane, 3-(meth)acryloxymethyl-3-ethyl oxetane, (3-ethyl-3-oxetanylmethoxy)methyl benzene, 4-fluoro-[1-(3-ethyl-3-oxetanylmethoxy)methyl]benzene, 4-methoxy-[1-(3-ethyl-3-oxetanylmethoxy)methyl]benzene, [1-(3-ethyl-3-oxetanylmethoxy)ethyl]phenyl ether, isobutoxymethyl (3-ethyl-3-oxetanylmethyl) ether, isobornyloxyethyl (3-ethyl-3-oxetanylmethyl) ether, isobornyl (3-ethyl-3-oxetanylmethyl) ether, 2-ethylhexyl (3-ethyl-3-oxetanylmethyl) ether, ethyl diethylene glycol (3-ethyl-3-oxetanylmethyl) ether, dicyclopentadiene (3-ethyl-3-oxetanylmethyl) ether, dicyclopentenyloxyethyl (3-ethyl-3-oxetanylmethyl) ether, dicyclopentenyl (3-ethyl-3-oxetanylmethyl) ether, tetrahydrofurfuryl (3-ethyl-3-oxetanylmethyl) ether, tetrabromophenyl (3-ethyl-3-oxetanylmethyl) ether, 2-tetrabromophenoxyethyl (3-ethyl-3-oxetanylmethyl) ether, tribromophenyl (3-ethyl-3-oxetanylmethyl) ether, 2-tribromophenoxyethyl (3-ethyl-3-oxetanylmethyl) ether, 2-hydroxyethyl (3-ethyl-3-oxetanylmethyl) ether, 2-hydroxypropyl (3-ethyl-3-oxetanylmethyl) ether, butoxyethyl (3-ethyl-3-oxetanylmethyl) ether, pentachlorophenyl (3-ethyl-3-oxetanylmethyl) ether, pentabromophenyl (3-ethyl-3-oxetanylmethyl) ether and bornyl (3-ethyl-3-oxetanylmethyl) ether.

Examples of a compound having two or more oxetanyl groups include, but are not limited to, polyfunctional oxetanes such as 3,7-bis(3-oxetanyl)-5-oxa-nonane, 3,3'-(1,3-(2-methylenyl)propanediylbis(oxymethylene))bis-(3-ethyloxetane), 1,4-bis[(3-ethyl-3-oxetanylmethoxy)methyl]benzene, 1,2-bis[(3-ethyl-3-oxetanylmethoxy)methyl]ethane, 1,3-bis[(3-ethyl-3-oxetanylmethoxy)methyl]propane, ethylene glycol bis(3-ethyl-3-oxetanylmethyl) ether, dicyclopentenylbis(3-ethyl-3-oxetanylmethyl) ether, triethylene glycolbis(3-ethyl-3-oxetanylmethyl) ether, tetraethylene glycolbis(3-ethyl-3-oxetanylmethyl) ether, tricyclodecanediyldimethylene(3-ethyl-3-oxetanylmethyl) ether, trimethylolpropanetris(3-ethyl-3-oxetanylmethyl) ether, 1,4-bis(3-ethyl-3-oxetanylmethoxy) butane, 1,6-bis(3-ethyl-3-oxetanylmethoxy) hexane, pentaerythritoltris(3-ethyl-3-oxetanylmethyl) ether, pentaerythritoltetrakis(3-ethyl-3-oxetanylmethyl) ether, polyethylene glycolbis(3-ethyl-3-oxetanylmethyl) ether, dipentaerythritolhexakis(3-ethyl-3-oxetanylmethyl) ether, dipentaerythritolpentakis(3-ethyl-3-oxetanylmethyl) ether, dipentaerythritoltetrakis(3-ethyl-3-oxetanylmethyl) ether, caprolactone-modified dipentaerythritolhexakis(3-ethyl-3-oxetanylmethyl) ether, caprolactone-modified dipentaerythritolpentakis(3-ethyl-3-oxetanylmethyl) ether, ditrimethylolpropanetetrakis(3-ethyl-3-oxetanylmethyl) ether, EO-modified bisphenol A bis(3-ethyl-3-oxetanylmethyl) ether, PO-modified bisphenol A bis(3-ethyl-3-oxetanylmethyl) ether, EO-modified hydrogenated bisphenol A bis(3-ethyl-3-oxetanylmethyl) ether, PO-modified hydrogenated bisphenol A bis(3-ethyl-3-oxetanylmethyl) ether and EO-modified bisphenol F (3-ethyl-3-oxetanylmethyl) ether.

The cationically polymerizable compounds may be used singly or in combinations of two or more. In the above, EO represents ethylene oxide, and an EO-modified compound means a compound having a block structure of an ethylene oxide group. PO represents propylene oxide, and a PO-modified compound means a compound having a block structure of a propylene oxide group. Further, hydrogenated means addition of a hydrogen atom(s) to a C=C double bond of a benzene ring or the like.

(2-2) A Photopolymerization Initiator (Component (B))

Then, a photopolymerization initiator being a component (B) will be described. The photopolymerization initiator is a substance to generate a reaction species to cause a polymerization reaction of a polymerizable compound (component (A)) by photostimulation. Specific examples thereof include photo-radical generating agents to generate a radical by photostimulation and photo-acid generating agents to generate a proton (H$^+$) by photostimulation.

The photo-radical generating agent is a polymerization initiator to generate a radical by light (infrared rays, visible light rays, ultraviolet rays, far ultraviolet rays, X rays, charged particle beams such as electron beams, and radiation), and is used mainly in the case where a polymerizable compound is a radically polymerizable compound. On the other hand, the photo-acid generating agent is a polymerization initiator to generate an acid (proton) by light, and is used mainly in the case where a polymerizable compound is a cationically polymerizable compound.

Examples of the photo-radical generating agent include, but are not limited to, 2,4,5-triarylimidazole dimers that may have a substituent, such as a 2-(o-chlorophenyl)-4,5-diphenylimidazole dimer, a 2-(o-chlorophenyl)-4,5-di(methoxyphenyl)imidazole dimer, a 2-(o-fluorophenyl)-4,5-diphenylimidazole dimer and a 2-(o- or p-methoxyphenyl)-4,5-diphenylimidazole dimer; benzophenone derivatives such as benzophenone, N,N'-tetramethyl-4,4'-diaminobenzophenone (Michler's ketone), N,N'-tetraethyl-4,4'-diaminobenzophenone, 4-methoxy-4'-dimethylaminobenzophenone, 4-chlorobenzophenone, 4,4'-dimethoxybenzophenone and 4,4'-diaminobenzophenone; aromatic ketone derivatives such as 2-benzyl-2-dimethylamino-1-(4-morpholinophenyl)-butanone-1,2-methyl-1-[4-(methylthio)phenyl]-2-morpholino-propanone-1-one; quinones such as 2-ethylanthraquinone, phenanthrene quinone, 2-t-butylanthraquinone, octamethylanthraquinone, 1,2-benzanthraquinone, 2,3-benzanthraquinone, 2-phenylanthraquinone, 2,3-dipheylanthraquinone, 1-chloroanthraquinone, 2-methylanthraquinone, 1,4-naphthoquinone, 9,10-phenanthraquinone, 2-methyl-1,4-naphthoquinone and 2,3-dimethylanthraquinone; benzoin ether derivatives such as benzoin methyl ether, benzoin ethyl ether and benzoin phenyl ether; benzoin derivatives such as benzoin, methyl benzoin, ethyl benzoin and propyl benzoin; benzyl derivatives such as benzyl dimethyl ketal; acridine derivatives such as 9-phenyl acridine and 1,7-bis(9,9'-acridinyl)heptane; N-phenyl glycine derivatives such as N-phenylglycine; acetophenone derivatives such as acetophenone, 3-methyl acetophenone, acetophenone benzyl ketal, 1-hydroxycyclohexyl phenyl ketone and 2,2-dimethoxy-2-phenyl acetophenone; thioxanthone derivatives such as thioxanthone, diethyl thioxanthone, 2-isopropyl thioxanthone and 2-chlorothioxanthone; xanthone, fluorenone, benzaldehyde, fluorene, anthraquinone, triphenylamine, carbazole, 1-(4-isopropylphenyl)-2-hydroxy-2-methylpropane-1-on, 2-hydroxy-2-methyl-1-phenylpropane-1-on, 2,4,6-trimethylbenzoyl diphenylphosphine oxide and bis-(2,6-dimethoxybenzoyl)-2,4,4-trimethylpentyl phosphine oxide. One of the photo-radical generating agents may be singly used or two or more of the radical generating agents may be used in combination.

Examples of commercially available products corresponding to the photo-radical generating agent include, but are not limited to, Irgacure 184, 369, 651, 500, 819, 907, 784 and 2959, CGI-1700, -1750 and -1850, CG24-61, and Darocur 1116 and 1173 (all manufactured by Ciba Japan K.K.), Lucirin TPO, LR8893 and LR8970 (all manufactured by BASF SE) and Ebecryl P36 (manufactured by UCB).

Examples of the photo-acid generating agent include, but are not limited to, onium salt compounds, sulfone compounds, sulfonate ester compounds, sulfoneimide compounds and diazomethane compounds. In the present invention, onium salt compounds are preferable.

The onium salt compound includes iodonium salts, sulfonium salts, phosphonium salts, dazonium salts, ammonium salts and pyridinium salts.

Specific examples of the onium salt compound include bis(4-t-butylphenyl)iodonium perfluoro-n-butane sulfonate, bis(4-t-butylphenyl)iodonium trifluoro methanesulfonate, bis(4-t-butylphenyl)iodonium 2-trifluoro methylbenzene sulfonate, bis(4-t-butylphenyl)iodonium pyrenesulfonate, bis(4-t-butylphenyl)iodonium n-dodecylbenzenesulfonate, bis(4-t-butylphenyl)iodonium p-toluenesulfonate, bis(4-t-butylphenyl)iodonium benzenesulfonate, bis(4-t-butylphenyl)iodonium 10-camphorsulfonate, bis(4-t-butylphenyl)iodonium n-octanesulfonate, diphenyliodonium perfluoro-n-butanesulfonate, diphenyliodonium trifluoro methanesulfonate, diphenyliodonium 2-trifluoro methylbenzene sulfonate, diphenyliodonium pyrenesulfonate, diphenyliodonium n-dodecyl benzenesulfonate, diphenyliodonium p-toluenesulfonate, diphenyliodnium benzenesulfonate, diphenyliodonium 10-camphorsulfonate, diphenyliodonium n-octanesulfonate, triphenylsulfonium perfluoro-n-butanesulfonate, triphenylsulfonium trifluoro methanesulfonate, triphenylsulfonium 2-trifluoromethylbenzenesulfonate, triphenylsulfonium pyrenesulfonate, triphenlsulfonium n-dodecylbenzenesulfonate, triphenylsulfonium p-toluenesulfonate, triphenylsulfonium benzenesulfonate, triphenylsulfonium 10-camphorsulfonate, triphenylsulfonium n-octanesulfonate, diphenyl(4-t-butylphenyl)sulfonium perfluoro-n-butanesulfonate, diphenyl(4-t-butylphenyl)sulfonium trifluoromethanesulfonate, diphenyl(4-t-butylphenyl)sulfonium 2-trifluoromethylbenzenesulfonate, diphenyl(4-t-butylphenyl)sulfonium pyrenesulfonate, diphenyl(4-t-butylphenyl) sulfonium n-dodecylbenzenesulfonate, diphenyl(4-t-butylphenyl)sulfonium p-toluenesulfonate, diphenyl(4-t-butylphenyl)sulfonium benzenesulfonate, diphenyl(4-t-butylphenyl)sulfonium 10-camphorsulfonate, diphenyl(4-t-butylphenyl)sulfonium n-octanesulfonate, tris(4-methoxyphenyl)sulfonium perfluoro-n-butanesulfonate, tris(4-methoxyphenyl)sulfonium trifluoromethanesulfonate, tris(4-methoxyphenyl)sulfonium 2-trifluoromethylbenzenesuflonate, tris(4-methoxyphenyl)sulfonium pyrenesulfonate, tris(4-methoxyphenyl)sulfonium n-dodecylbenzenesulfonate, tris(4-methoxyphenyl)sulfonium p-toluenesulfonate, tris(4-methoxyphenyl)sulfonium benzenesulfonate, tris(4-methoxyphenyl)sulfonium 10-camphorsulfonate and tris(4-methoxyphenyl)sulfonium n-octanesulfonate.

Examples of the sulfone compound include β-ketosulfone, β-sulfonylsulfone and α-diazo compounds of these. Specific examples of the sulfone compound include, but are not limited to, phenacylphenyl sulfone, mesityl phenacyl sulfone, bis(phenylsulfonyl)methane and 4-trisphenacyl sulfone.

Examples of the sulfonate compound include alkyl sulfonate, haloalkyl sulfonate, aryl sulfonate and iminosulfonate. Specific examples of the sulfonate compound include, but are not limited to, α-methylolbenzoin perfluoro-n-butane sulfonate, α-methylolbenzoin trifluoromethane sulfonate and α-methylolbenzoin 2-trifluoromethyl benzene sulfonate.

Specific examples of the sulfonimide compound include, but are not limited to, N-(trifluoromethylsulfonyloxy)succinimide, N-(trifluoromethylsulfonyloxy)phthalimide, N-(trifluoromethylsulfonyloxy)diphenylmaleimide, N-(trifluoromethylsulfonyloxy)bicyclo[2.2.1]hept-5-en-2,3-dicarboxyimide, N-(trifluoromethylsulfonyloxy)-7-oxabicyclo[2.2.1]hept-5-en-2,3-dicarboxyimide, N-(trifluoromethylsulfonyloxy)bicyclo[2.2.1]heptane-5,6-oxy-2,3-dicarboxyimide, N-(trifluoromethylsulfonyloxy) naphthylimide, N-(10-camphorsulfonyloxy)succinimide, N-(10-camphorsulfonyloxy)phthalimide, N-(10-camphorsulfonyloxy)diphenylmaleimide, N-(10-camphorsulfonyloxy)bicyclo[2.2.1]hept-5-en-2,3-dicarboxyimide, N-(10-camphorsulfonyloxy)-7-oxabicyclo[2.2.1]hept-5-en-2,3-dicarboxyimide, N-(10-camphorsulfonyloxy)bicyclo[2.2.1]heptane-5,6-oxy-2,3-dicarboxyimide, N-(10-camphorsulfonyloxy)naphthylimide, N-(4-methylphenylsulfonyloxy) succinimide, N-(4-methylphenylsulfonyloxyl)phthalimide, N-(4-methylphenylsulfonyloxy)diphenylmaleimide, N-(4-methylphenylsulfonyloxyl)bicyclo[2.2.1]hept-5-en-2,3-dicarboxyimide, N-(4-methylphenylsulfonyloxy)-7-oxabicyclo[2.2.1]hept-5-en-2,3-dicarboxyimide, N-(4-methylphenylsulfonyloxyl)bicyclo[2.2.1]heptane-5,6-oxy-2,3-dicarboxyimide, N-(4-methylphenylsulfonyloxyl) naphthylimide, N-(2-trifluoromethylphenylsulfonyloxy) succinimide, N-(2-trifluoromethylphenylsulfonyloxyl) phthalimide, N-(2-trifluoromethylphenylsulfonyloxy)diphenylmaleimide, N-(2-trifluoromethylphenylsulfonyloxyl)bicyclo[2.2.1]hept-5-en-2,3-dicarboxyimide, N-(2-trifluoromethylphenylsulfonyloxy)-7-oxabicyclo[2.2.1]hept-5-en-2,3-dicarboxyimide, N-(2-trifluoromethylphenylsulfonyloxyl)bicyclo[2.2.1]heptane-5,6-oxy-2,3-dicarboxyimide, N-(2-trifluoromethylphenylsulfonyloxy) naphthylimide, N-(4-fluorophenylsulfonyloxy) succinimide, N-(4-fluorophenyl) phthalimide, N-(4-fluorophenylsulfonyloxy) diphenylmaleimide, N-(4-fluorophenylsulfonyloxyl)bicyclo[2.2.1]hept-5-en-2,3-dicarboxyimide, N-(4-fluorophenylsulfonyloxy)-7-oxabicyclo[2.2.1]hept-5-en-2,3-dicarboxyimide, N-(4-fluorophenylsulfonyloxyl)bicyclo[2.2.1]heptane-5,6-oxy-2,3-dicarboxyimide and N-(4-fluorophenylsulfonyloxyl)naphthylimide.

Specific examples of the diazomethane compound include, but are not limited to, bis(trifluoromethylsulfonyl) diazomethane, bis(cyclohexylsulfonyl)diazomethane, bis (phenylsulfonyl)diazomethane, bis(p-toluenesulfonyl)diazomethane, methylsulfonyl p-toluenesulfonyl diazomethane, (cyclohexylsulfonyl) (1,1-dimethylethylsulfonyl)diazomethane and bis(1,1-dimethylethylsulfonyl)diazomethane.

In the present invention, the photopolymerization initiator being a component (B) may be used singly or as a mixture of two or more.

The content of a photopolymerization initiator (component (B)) contained in a photocurable composition is not limited, but in use for nanoimprint lithography, is preferably 0.01 wt % or more and 10 wt % or less, more preferably 0.1 wt % or more and 7 wt % or less, and especially preferably 0.5 wt % or more and 5 wt % or less, based on the weight of a polymerizable compound (component (A)). If the content is in this range, it is likely that the generation speed of a gas is fast, and bubbling in the interior of a cured film is hardly caused. By contrast, if the content of a component (B) is less than 0.01 wt % based on the weight of a component (A), it may possibly be caused that a gas is generated before a photocurable composition is fully cured, and bubbling is caused in the interior of the photocurable composition. If the content of a component (B) exceeds 10 wt % based on the weight of a component (A), since the amount of light absorption of an initiator becomes large, the light absorption of a gas generating agent is likely to be inhibited to thereby retard the generation speed of a gas.

As described hitherto, the photocurable composition according to the present invention has, at least, a polymerizable compound (component (A)), a polymerization initiator (component (B)) and a photosensitive gas generating agent (component (C)). However, in addition to these three components, the photocurable composition may contain at least one of a surfactant (D) and additives in a range not spoiling the advantageous effects of the present invention according to various purposes.

(2-3) A Surfactant (Component (D))

Since the incorporation of a surfactant (component (D)) in a photocurable compound in addition to the above three components, allows reduction of an interface bonding force between a mold and a resist, the effect of reducing the mold releasing force by a photosensitive gas generating agent (component (C)) can be further enhanced.

The surfactants (component (D)) usable are a silicone-based surfactant and a fluorine-based surfactant. A fluorine-based surfactant is preferable from the viewpoint of being excellent in the effect of reducing the mold releasing force. In the present invention, the surfactant (component (D)) exhibits no polymerizability. In the present invention, the surfactant has no photostimulation responsive gas generating group.

The fluorine-based surfactant includes polyalkylene oxide (polyethylene oxide, polypropylene oxide or the like) adducts of alcohols having a perfluoroalkyl group and polyalkylene oxide (polyethylene oxide, polypropylene oxide or the like) adducts of perfluoropolyethers. Here, the fluorine-based surfactant may have a hydroxyl group, an alkyl group, an amino group, a thiol group and the like in a part (for example, an end group) of the molecule structure. The surfactants usable may be commercially available surfactants.

A surfactant (component (D)) may be a hydrocarbon-based surfactant.

The hydrocarbon-based surfactant includes alkyl alcohol polyalkylene oxide adducts in which an alkylene oxide having 2 to 4 carbon atoms is added to an alkyl alcohol having 1 to 50 carbon atoms.

The alkyl alcohol polyalkylene oxide adducts include methyl alcohol ethylene oxide adducts, decyl alcohol ethylene oxide adducts, lauryl alcohol ethylene oxide adducts, cetyl alcohol ethylene oxide adducts, stearyl alcohol ethylene oxide adducts and stearyl alcohol ethylene oxide/propylene oxide adducts. Here, end groups of the alkyl alcohol polyalkylene oxide adducts are not limited to hydroxyl groups produced by simply adding polyalkylene oxides to alkyl alcohols. The hydroxyl groups may be converted to other substituents, for example, polar functional groups such as a carboxyl group, an amino group, a pyridyl group, a thiol group and a silanol group, and hydrophobic functional groups such as an alkyl group.

The alkyl alcohol polyalkylene oxide adducts usable may be commercially available products. Examples of the commercially available product include polyoxyethylene methyl ethers made by Aoki Oil Industrial Co., Ltd. (methyl alcohol ethylene oxide adducts) (BLAUNON MP-400, BLAUNON MP-550 and BLAUNON MP-1000), polyoxyethylene decyl ethers made by Aoki Oil Industrial Co., Ltd. (decyl alcohol ethylene oxide adducts) (FINESURF D-1303, FINESURF D-1305, FINESURF D-1307 and FINESURF D-1310), a polyoxyethylene lauryl ether made by Aoki Oil Industrial Co., Ltd. (lauryl alcohol ethylene oxide adduct) (BLAUNON EL-1505), polyoxyethylene cetyl ethers made by Aoki Oil Industrial Co., Ltd. (cetyl alcohol ethylene oxide adducts) (BLAUNON CH-305 and BLAUNON CH-310) and polyoxyethylene stearyl ethers made by Aoki Oil Industrial Co., Ltd. (stearyl alcohol ethylene oxide adducts) (BLAUNON SR-705, BLAUNON SR-707, BLAUNON SR-715, BLAUNON SR-720, BLAUNON SR-730 and BLAUNON SR-750).

The surfactant being a component (D) may be used singly or as a mixture of two or more.

In the case of incorporating a surfactant being a component (D) in the photocurable composition according to the present invention, the content of the surfactant is, for example, 0.001 wt % to 10 wt %, preferably 0.01 wt % to 7 wt %, and more preferably 0.05 wt % to 5 wt %, based on the total weight of a polymerizable compound (component (A)) and a photosensitive gas generating agent (component (C)). Setting the content at least in the range of 0.001 wt % to 10 wt % brings about the effect of reducing the mold releasing force on the photocurable composition and also gives the effect of being excellent in the filling property.

(2-4) Additives

Additives include a sensitizing agent, an antioxidant, a solvent and a polymer component.

Incorporation of a sensitizing agent is likely to accelerate the polymerization reaction and improve the reaction conversion rate. The sensitizing agent includes hydrogen donors and sensitizing dyes.

A hydrogen donor is a compound to donate hydrogen to an initiation radical generated from a polymerization initiator (component (B)) and a radical of a polymerization growing end, and to by itself generate a radical. If a hydrogen donor is added in the case where a polymerization initiator (component (B)) is a photo-radical generating agent, the polymerization speed is improved in some cases.

Specific examples of the hydrogen donor include, but are not limited to, amine compounds such as N-butylamine, di-n-butylamine, tri-n-butylphosphine, allylthiourea, s-benzylisothiuronium-p-toluene sulfinate, triethylamine, diethylaminoethyl methacrylate, triethylenetetramine, 4,4'-bis(dialkylamino)benzophenone, ethyl N,N-dimethylaminobenzoate, isoamyl N,N-dimethylaminobenzoate, pentyl-4-dimethyl aminobenzoate, triethanolamine and N-phenylglycine, and mercapto compounds such as 2-mercapto-N-phenylbenzimidazole and mercaptopropionate esters.

A sensitizing dye is a compound to absorb light of a specific wavelength to be thereby excited, and to act on a polymerization initiator (component (B)). The action used here involves the energy transfer, the electron transfer and the like from the sensitizing dye in an excited state to the polymerization initiator (component (B)). If a sensitizing agent is added in the case where a polymerization initiator (component (B)) is a photo-radical generating agent, the polymerization speed is improved in some cases.

Specific Examples of the sensitizing dye include, but are not limited to, anthracene derivatives, anthraquinone derivatives, pyrene derivatives, perylene derivatives, carbazole derivatives, benzophenone derivatives, thioxanthone derivatives, xanthone derivatives, thioxanthone derivatives, coumalin derivatives, phenothiazine derivatives, camphorquinone derivatives, acridine-based dyes, thiopyrylium salt-based dyes, merocyanine-based dyes, quinoline-based dyes, styrylquinoline-based dyes, ketocoumalin-based dyes, thioxanthene-based dyes, xanthene-based dyes, oxonol-based dyes, cyanine-based dyes, rhodamine-based dyes and pyrylium salt-based dyes.

The sensitizing agent can be used singly or as a mixture of two or more.

In the case of containing a sensitizing agent, the content of the sensitizing agent is preferably 10 wt % or less, and more preferably 0.1 wt % to 5 wt %, based on the weight of a polymerizable compound (A). Making the content of a sensitizing agent to be 0.1 wt % or more enables more effectively developing the effect of the sensitizing agent. If the content of a sensitizing agent is made to be 10 wt % or less, the solubility and the preservation stability are likely to be excellent.

The polymer component includes vinyl polymers (polystyrene and the like), and polyalkylene glycols (polyethylene glycol, polypropylene glycol and the like). Incorporation of a polymer component enables regulating the solubility of a condensable gas described later and the effect of reducing the mold releasing force.

Then, suitable conditions of preparing a photocurable composition will be described.

<Temperature when a Photocurable Composition is Blended>

When a photocurable composition is prepared by mixing and dissolving reagents and a solvent, the preparation is carried out under a predetermined temperature condition. Specifically, the preparation is carried out in the range of 0° C. to 100° C. The temperature is preferably 10° C. to 50° C. from the viewpoint of workability and the like.

<Viscosity of a Photocurable Composition>

The viscosity of the photocurable composition according to the present invention, as a viscosity at 23° C. of a mixture of components thereof excluding the solvent, is preferably 1 cP to 100 cP, more preferably 5 cP to 50 cP, and still more preferably 6 cP to 20 cP. If the viscosity of a photocurable composition is higher than 100 cP, in some cases where the photocurable composition is used for nanoimprint lithography, a long time is needed for the photocurable composition to be filled in recesses of a fine pattern on a mold when the composition contacts with the mold, and pattern defects are caused due to filling faults. By contrast if the viscosity is lower than 1 cP, some cases arise where the coating unevenness is caused when a photocurable composition is applied, and the photocurable composition flows out from ends of a mold when the photocurable composition contacts with the mold.

<Surface Tension of a Photocurable Composition>

The surface tension of the photocurable composition according to the present invention, as a surface tension at 23° C. of a mixture of components thereof excluding the solvent, is preferably 5 mN/m to 70 mN/m, more preferably 7 mN/m to 35 mN/m, and still more preferably 10 mN/m to 32 mN/m. If the surface tension is lower than 5 mN/m, a long time is needed for the photocurable composition to be filled in recesses of a fine pattern on a mold when the composition contacts with the mold. By contrast, if the surface tension is higher than 70 mN/m, the surface smoothness becomes low.

<Impurities Such as Particles Mixed in a Photocurable Composition>

It is desirable that impurities such as particles are removed as much as possible from the photocurable composition according to the present invention. In order to prevent, for example, particles contaminating a photocurable composition from carelessly producing irregularities on a photocured product and generating pattern defects, it is desirable that impurities such as particles are removed. Specifically, after each component contained in a photocurable composition is mixed, the mixture is preferably filtered, for example, with a filter having a pore size of 0.001 µm to 5.0 µm. When the filtration is carried out using a filter(s), the filtration is more preferably carried out in multiple stages or repeated multiple times. A filtrate liquid may be again filtered. A filter usable for the filtration is a polyethylene resin-made, polypropylene resin-made, fluororesin-made, nylon resin-made filters or the like, but is not especially limited.

Here, in the case where the photocurable composition according to the present invention is used for manufacture of semiconductor integrated circuits, in order not to inhibit the operation of products, contamination of the composition with metal impurities can be avoided to the utmost. Therefore, in the photocurable composition according to the present invention, the concentration of metal impurities contained in the composition is preferably 10 ppm or less, and more preferably 100 ppb or less.

[Method for Forming a Film]

Then, the method for forming a film according to the present invention will be described. Here, the method for forming a film mentioned in the present invention includes a photo-imprinting method. The photo-imprinting method is defined preferably as a method for forming a pattern of 1 nm to 10 mm in size. More preferably, the photo-imprinting method means a method for forming a pattern of about 10 nm to 100 µm in size. On the other hand, a technology of forming a pattern having the pattern (protruding and recessed structure) in nano-size (1 nm to 100 nm) is called photo-nanoimprint, and the method for forming a film according to the present invention naturally includes a photo-nanoimprint method.

FIGS. 1A to 1F are cross-sectional schematic diagrams illustrating examples of an embodiment in the production method of a film according to the present invention. The production process illustrated in FIGS. 1A to 1F is a production process including steps described in the following [1] to [5] or [6].

Figure 1C:
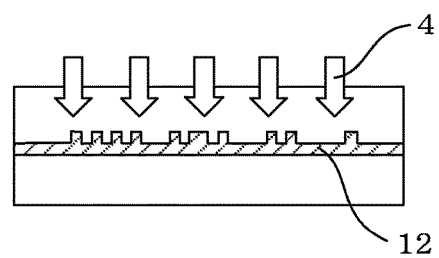
FIG. 1C is a cross-sectional schematic diagram illustrating an example of the embodiment in the production method of a film according to the present invention.
Figure 1D:
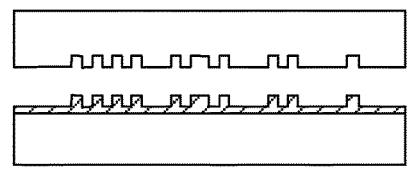
FIG. 1D is a cross-sectional schematic diagram illustrating an example of the embodiment in the production method of a film according to the present invention.
Figure 1E:
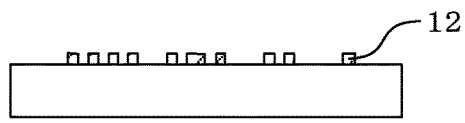
FIG. 1E is a cross-sectional schematic diagram illustrating an example of the embodiment in the production method of a film according to the present invention.
Figure 1F:
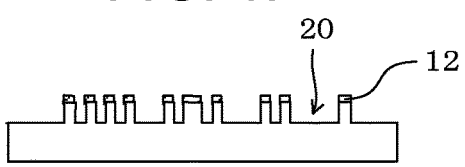
FIG. 1F is a cross-sectional schematic diagram illustrating an example of the embodiment in the production method of a film according to the present invention.

[1] A disposing step (applying step, FIG. 1A)
[2] A mold contact step (FIGS. 1B1 and 1B2)
[3] A light irradiation step (FIG. 1C)
[4] A mold releasing step (FIG. 1D)
[5] A remaining film removing step (FIG. 1E)
[6] A substrate processing step (FIG. 1F)

Through the steps described in [1] to [6](or the steps described in [1] to [5]) in the above, a photocured product 12, and an electronic component (electronic device) or an optical component having the photocured product 12 are obtained from a photocurable composition 1. Hereinafter, details of the each step will be described.

<Disposing Step (FIG. 1A)>

First, the photocurable composition 1 is disposed (applied) on a substrate 2 to thereby form a coating film (FIG. 1A). The photocurable composition used here is the photocurable composition according to the present invention.

As a substrate to be processed corresponding to the substrate 2, a silicon wafer is usually used, but the substrate to be processed is not limited thereto. A substrate to be processed can be optionally selected and used from among substrates, known as substrates for semiconductor devices, of aluminum, a titanium-tungsten alloy, an aluminum-silicon alloy, an aluminum-copper-silicon alloy, silicon oxide, silicon nitride or the like, in addition to the silicon wafer. Here, a substrate improved in the adhesion with a photocurable composition by a surface treatment such as a silane coupling treatment, a silazane treatment or the formation of an organic thin film may be used as a substrate to be processed.

A method usable for disposing the photocurable composition according to the present invention on a substrate to be processed can be, for example, an inkjet method, a dip coat method, an air knife coat method, a curtain coat method, a wire bar coat method, a gravure coat method, an extrusion coat method, a spin coat method or a slit scan method. Here, the film thickness of a shape-transferred layer (coating film) depends on usage applications, but is, for example, 0.01 µm to 100 µm.

<Mold Contact Step (FIGS. 1B1 and 1B2)>

Then, a step (mold contact step, FIGS. 1B1 and 1B2) is carried out which brings a mold into contact with the coating film of the photocurable composition 1 formed in the previous step (the disposing step). Here, since a mold 3 can be regarded as a seal, this step is also called a stamping step. In the present step, by bringing the mold 3 into contact with the photocurable composition 1 (shape-transferred layer) (FIG. 1B1), (a part of) a coating film 11 is filled in recesses of a fine pattern formed on the mold 3 (FIG. 1B2).

The mold 3 used in the mold contact step needs to be constituted of an optically transparent material in consideration of the succeeding step (light irradiation step). The constituting material of the mold 3 specifically includes glass, quartz, optically transparent resins such as PMMA (poly(methyl methacrylate)) and polycarbonate resins, transparent metal deposited films, flexible films of polydimethylsiloxane, photocured films and metal films. However, in the case where an optically transparent resin is used as the constituting material of the mold 3, the resin not dissolving in a solvent contained in the photocurable composition 1 needs to be selected. The surface of the mold contacting with the photocurable composition is preferably hydrophilic, and is especially preferably a quartz surface, for the reason that the polar bonds (hydrogen bond and ionic bond etc.) with polar functional groups being substituents contained in a surfactant being a component (D) are easily formed.

The mold 3 used in the method for producing a photocured product according to the present invention may be a mold having been subjected to a surface treatment in order to improve the detachability between the photocurable composition 1 and the surface of the mold 3. A method of the surface treatment includes a method of applying a mold releasing agent on the surface of the mold to form a mold releasing agent layer before the mold contact step is carried out. Here, a mold releasing agent applied on the surface of a mold includes silicon-based mold releasing agents, fluorine-based mold releasing agents, polyethylene-based mold releasing agents, polypropylene-based mold releasing agents, paraffin-based mold releasing agents, montan-based mold releasing agents and carnauba-based mold releasing agents. Commercially available coating-type mold releasing agents, for example, Optool DSX made by Daikin Industries, Ltd. can suitably be used. The mold releasing agents may be used singly or in combinations of two or more. Among these, fluorine-based mold releasing agents are especially preferable.

In the mold contact step, when the mold 3 is brought into contact with the photocurable composition 1 as illustrated in FIG. 1B1, the pressure applied on the photocurable composition 1 is not especially limited, but is usually 0.1 MPa to 100 MPa. Among these pressures, the pressure is preferably 0.1 MPa to 50 MPa, more preferably 0.1 MPa to 30 MPa, and still more preferably 0.1 MPa to 20 MPa. Further in the mold contact step, the time in which the mold 3 is brought into contact with the shape-transferred layer 1 is not especially limited, but is usually 0.1 sec to 600 sec, preferably 0.1 sec to 300 sec, more preferably 0.1 sec to 180 sec, and especially preferably 0.1 sec to 120 sec.

The mold contact step can be carried out under any condition of an ambient atmosphere, a depressurized atmosphere and an inert gas atmosphere. The depressurized atmosphere and the inert gas atmosphere are preferable because the influence of oxygen and moisture on the photocuring reaction can be prevented. In the case where the mold contact step is carried out under an inert gas atmosphere, specific examples of an inert gas to be used include nitrogen, carbon dioxide, helium, argon, various flon gases and mixed gases thereof. In the case where the present step (mold contact step) is carried out under a specific gas atmosphere including an ambient atmosphere, the pressure can be 0.0001 atm to 10 atm. Here, a depressurized atmosphere and an inert gas atmosphere are preferable because the influence of oxygen and moisture on the photocuring reaction can be prevented.

The mold contact step may be carried out under an atmosphere containing a condensable gas (hereinafter, condensable gas atmosphere). In the present invention and the present description, the condensable gas is defined as a gas which is present as a gas in the atmosphere before the photocurable composition 1 (shape-transferred layer) and the mold 3 are brought into contact with each other (FIG. 1B1), and condenses and liquefies by a capillary pressure generated by a pressure in the filling time when the photocurable composition 1 (shape-transferred layer) and the mold 3 are brought into contact with each other and the gas in the atmosphere is filled in recesses of a fine pattern formed on the mold 3 and in gaps between the mold and the substrate together with (a part of) the coating film 11, in the mold contact step.

If the mold contact step is carried out under the condensable gas atmosphere, since the gas filled in the recesses of the fine pattern liquefies to thereby vanish bubbles, the filling property is excellent. The condensable gas may be dissolved in the curable composition.

The boiling point of a condensable gas is not limited as long as being an atmospheric temperature or lower of the mold contact step, but is preferably −10° C. to 23° C., and more preferably 10° C. to 23° C. If the boiling point is in this range, the filling property is better.

The vapor pressure of the condensable gas at an atmospheric temperature in the mold contact step is not limited as long as being a molding pressure when the stamping is carried out in the mold contact step or a lower pressure, but can be 0.1 to 0.4 MPa. If the vapor pressure is in this range, the filling property is better. If the vapor pressure at an atmospheric temperature is higher than 0.4 MPa, the effect of vanishing bubbles is unlikely to be attained sufficiently. By contrast, if the vapor pressure at an atmospheric temperature is lower than 0.1 MPa, depressurization is needed and the apparatus is likely to become complicated.

The atmospheric temperature of the mold contact step is not especially limited, but can be 20° C. to 25° C.

The condensable gas specifically includes flons including chlorofluorocarbons (CFC) such as trichlorofluoromethane, fluorocarbons (FC), hydrochlorofluorocarbons (HCFC), hydrofluorocarbons (HFC) such as 1,1,1,3,3-pentafluoropropane ($CHF_2CH_2CF_3$, HFC-245fa, PFP), and hydrofluoroethers (HFE) such as pentafluoroethyl methyl ether ($CF_3CF_2OCH_3$, HFE-245mc).

Among these, 1,1,1,3,3-pentafluoropropane (vapor pressure at 23° C.: 0.14 MPa, boiling point: 15° C.), trichlorofluoromethane (vapor pressure at 23° C.: 0.1056 MPa, boiling point: 24° C.) and pentafluoroethyl methyl ether are preferable, from the viewpoint that the filling property at an atmospheric temperature of 20° C. to 25° C. in the mold contact step is excellent; and 1,1,1,3,3-pentafluoropropane is especially preferable from the viewpoint of being excellent in the safety.

The condensable gas may be used singly or as a mixture of two or more. The condensable gas may be used as a mixture with a non-condensable gas such as air, nitrogen, carbon dioxide, helium and argon. The non-condensable gas to be mixed with a condensable gas is preferably helium from the viewpoint of the filling property. If the non-condensable gas is helium, since when the gases (the condensable gas and helium) in the atmosphere is filled in recesses of a fine pattern formed on the mold 3 together with (a part of) the coating film 11 in the mold contact step, the condensable gas liquefies and helium simultaneously permeates the mold, the filling property is excellent.

<Light Irradiation Step (FIG. 1C)>

Then, the coating film 11 is irradiated with light through the mold 3 (FIG. 1C). In this step, the coating film 11 is cured with the irradiated light to thereby form a photocured product 12.

Here, the light used for irradiating the photocurable composition 1 constituting the coating film 11 is selected according to the sensitivity wavelength of the photocurable composition 1, but can suitably be selected and used specifically from ultraviolet light of about 150 nm to 400 nm in wavelength, X-rays and electron beams. Here, many of commercially available products as curing aids (photopolymerization initiators) are compounds having a sensitivity to ultraviolet light. For this reason, light (irradiation light 4) used for irradiating the photocurable composition 1 is especially preferably ultraviolet light. Examples of light sources emitting ultraviolet light include high-pressure mercury lamps, ultrahigh-pressure mercury lamps, low-pressure mercury lamps, Deep-UV lamps, carbon arc lamps, chemical lamps, metal halide lamps, xenon lamps, KrF excimer lasers, ArF excimer lasers and $F_2$ excimer lasers, but ultrahigh-pressure mercury lamps are especially preferable. The number of light sources may be one or plural. When the light irradiation is carried out, the light irradiation may be carried out on the whole surface of the photocurable composition 1, or on a partial region thereof.

Further in the case where the shape-transferred layer is cured also by heat, heat curing may be further carried out. In the case where the heat curing is carried out, the heating atmosphere, the heating temperature and the like are not especially limited. For example, in an inert atmosphere or under reduced pressure, the photocurable composition 1 can be heated in the range of 40° C. to 200° C. When the shape-transferred layer 1 is heated, a hot plate, an oven, a furnace or the like can be used.

<Mold Releasing Step (FIG. 1D)>

Then, a step (mold releasing step, FIG. 1D) in which the mold 3 is removed from the photocured product 12 and a cured film having a predetermined pattern shape is formed on the substrate 2 is carried out. This step (mold releasing step) is a step of detaching the mold 3 from the photocured product 12, whereby a reversal pattern of the fine pattern formed on the mold 3 in the previous step (light irradiation step) is obtained as a pattern of the photocured product 12.

In the case where the mold contact step is carried out under a condensable gas atmosphere, when the cured film and the mold are separated in the mold releasing step, the condensable gas vaporizes along with a decrease in the pressure at the interface where the cured film and the mold contact each other, whereby the effect of reducing the mold releasing force is likely to be attained.

A method for detaching the mold 3 from the photocured product 12 is not especially limited unless physically damaging a part of the photocured product 12 in the detaching, and also various conditions and the like are not especially limited. For example, the substrate to be processed (substrate 2) may be fixed and the mold 3 may be moved away and detached from the substrate to be processed; the mold 3 may be fixed and the substrate to be processed may be moved away and detached from the mold; or the both may be drawn in the exact opposite directions and detached from each other.

<Remaining Film Removing Step (FIG. 1E)>

Although the cured film obtained in the above mold releasing step has a specific pattern shape, a part of the film is sometimes present as a remaining film also on a region other than a region where the pattern shape is formed. Then, a step (remaining film removing step, FIG. 1E) is carried out which removes the remaining photocured film (remaining film) in the region where the photocured product needs to be removed, from the above pattern shape.

Examples of a method for removing the remaining film include a method in which the film (remaining film) remaining in recesses of the photocured product 12 is removed by etching and surfaces of the substrate 2 are exposed in pattern recesses.

In the case of utilizing etching, a specific method thereof is not especially limited, and a conventionally known method, for example, dry etching can be used. The dry etching can use a conventionally known dry etching apparatus. A source gas usable in dry etching is suitably selected according to the element composition of a film to be etched, but may be a gas containing oxygen atoms such as $O_2$, CO and $CO_2$, an inert gas such as He, $N_2$ and Ar, a chlorine-based gas such as $Cl_2$ and $BCl_3$, or a gas such as $H_2$ and $NH_3$. Here, these gases may be mixed and used.

By the above production process of [1] to [5], the photocured product 12 having a desired protruding and recessed pattern shape (pattern shape originated from the protruding and recessed shape of the mold 3) can be obtained. Here, in some cases where the substrate 2 is processed by utilizing the photocured product 12, a processing step described later of the substrate may further be carried out.

Meanwhile, the obtained photocured product 12 can be utilized as an optical member (including cases of being used as one member of optical members). In such a case, the optical member can be provided as an optical member having, at least, the substrate 2 and the photocured product 12 disposed on the substrate 2.

<Substrate Processing Step (FIG. 1F)>

The photocured product 12 having a desired protruding and recessed pattern shape obtained by the production method according to the present invention can be utilized, for example, as films for interlayer insulating films contained in electronic components represented by semiconductor devices such as LSI, system LSI, DRAM, SDRAM, RDRAM and D-RDRAM. On the other hand, the photocured product 12 can also be utilized as resist films in production of semiconductor devices.

In the case where the photocured product 12 is utilized as a resist film, specifically, as illustrated in FIG. 1F, etching, ion implantation or the like is carried out on a part (region of reference numeral 20) of the substrate whose surface is exposed in an etching step. Here, the photocured product 12 at this time functions as a mask. Thereby, a circuit structure (not shown) based on the pattern shape of the photocured product 12 can be formed on the substrate 2. Thereby, a substrate with a circuit utilized in semiconductor devices and the like can be produced. Here, by installing electronic members on the substrate with a circuit, an electronic component is formed.

In the case of fabricating substrates with a circuit and electronic components, the pattern of the photocured product may finally be removed from the processed substrate, but the pattern can be left as a member constituting a device.

Effects of the photosensitive gas generating agent according to the present invention, attained by each step of the production process of a film by nanoimprint lithography, are considered as described below.

In the disposing step, the effect of hydrophobicity of the perfluoroalkyl group makes the photosensitive gas generating agent to be unevenly distributed at the gas-liquid interface of the photocurable composition 1 disposed on the substrate to be processed (substrate 2).

Then, in the succeeding mold contact step, the polyalkyleneoxy group having affinity for the surface of the mold (mold 3) makes the photosensitive gas generating agent to be unevenly distributed at the contact interface between the photocurable composition and the mold when the photocurable composition 1 and the mold are brought into contact with each other.

Then, in the succeeding light irradiation step, the effect of a pressure by a gas generated from the photosensitive gas generating agent breaks the interfacial bond between the mold (mold 3) and the cured product 11 of the photocurable composition to thereby reduce the mold releasing force. Accumulation of a gas generated after the interfacial bond has been broken between the cured product 11 of the photocurable composition and the mold further produces a gas-liquid interface. The perfluoroalkyl group of the photosensitive gas generating agent is resultantly unevenly distributed at the gas-liquid interface. The hydrophobicity of the perfluoroalkyl group thereby serves to prevent the re-adhesion of the mold with the cured product 11 of the photocurable composition. Here, the re-adhesion of the mold with the cured product 11 is a phenomenon in which the gas generated at the interface between the mold and the cured product 11 escapes from the interface, and the mold and the cured product 11 are again adhered.

The above-mentioned effect of the formation of the gas-liquid interface by the gas, and the above-mentioned effect of the hydrophobicity of the perfluoroalkyl group contained in the photosensitive gas generating agent reduce the mold releasing force needed when the mold is separated from the substrate provided with the cured product 11 in the mold releasing step. Here, in order to reduce the mold releasing force, it is important that the amount of the gas generated at the gas-liquid interface is made large and the adhesion force between the cured product 11 of the photocurable composition and the mold is reduced. At this point, the photosensitive gas generating agent according to the present invention, since being likely to be unevenly distributed at the interface between the cured product 11 and the surface of the mold, can generate a gas effectively at the interface between the cured product 11 and the surface of the mold, and can reduce the adhesion force when the cured product 11 and the mold are re-adhered.

From the above, the photocurable composition containing the photosensitive gas generating agent according to the present invention is an excellent composition capable of reducing the mold releasing force even in a small amount of light exposure. Therefore, if the photosensitive gas generating agent according to the present invention is used as a material for nanoimprint lithography, a photocurable composition exhibiting a high productivity and a method for producing a film using the photocurable composition can be provided. The photosensitive gas generating agent according to the present invention may also be used as a foaming agent to produce foamed bodies.

EXAMPLES

Hereinafter, the present invention will be described in detail by way of Examples, but the technical scope of the present invention is not limited to Examples described below. [Parts] and [%] used in the following descriptions are units in terms of weight unless otherwise specified.

Example 1

Synthesis of a Photosensitive Gas Generating Agent (C1)

2H,2H-perfluorooctyl alcohol ethylene oxide-5-mol adduct (made by DIC Corp.): 50 parts
Triethylamine: 23.7 parts
Dichloromethane: 500 parts Then, 21.2 parts of para-toluenesulfonyl chloride was further added while the reaction solution was being stirred, and thereafter stirred further for 18 hours. Then, 500 ml of water was added to the reaction solution in a suspension state, and thereafter, an organic layer was extracted with chloroform, and dried. Then, the organic layer was concentrated under reduced pressure to thereby obtain a crude product. Then, the crude product was purified with silica gel column chromatography to thereby obtain 63.5 parts of a reaction intermediate X1.

(2) Synthesis of a Reaction Intermediate X2

After the interior of a reaction vessel is put in a nitrogen atmosphere, the following reagent and solvent were charged in the reaction vessel at room temperature. The reaction intermediate X1: 63.5 parts
Ethylamine: 500 parts Then, the reaction solution was stirred for 18 hours at room temperature. Then, 700 parts of a sodium hydrogencarbonate aqueous solution was added to a residue obtained by concentrating the reaction solution under reduced pressure, and thereafter, an organic layer was extracted with

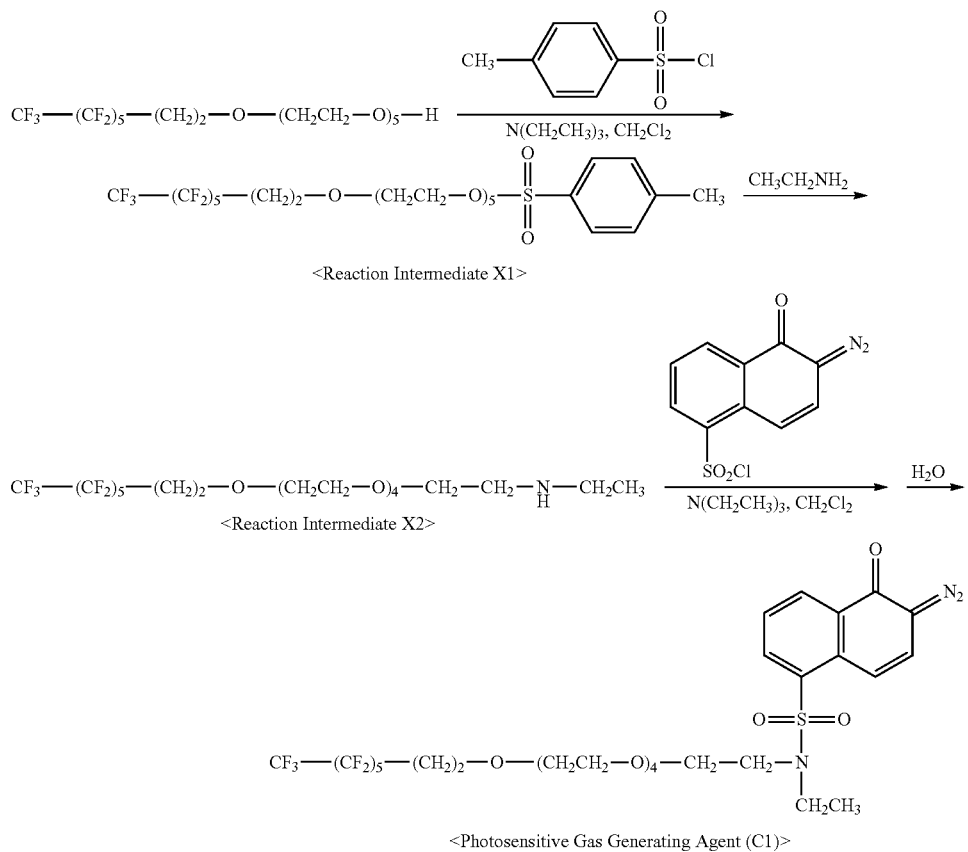

(1) Synthesis of a Reaction Intermediate X1

After the interior of a reaction vessel is put in a nitrogen atmosphere, the following reagents and solvent were charged in the reaction vessel at room temperature. 1H,1H, chloroform, and dried. Then, the organic layer was concentrated under reduced pressure to thereby obtain a crude product. Then, the crude product was purified with silica gel column chromatography to thereby obtain 52.6 parts of a reaction intermediate X2.

(3) Synthesis of a Photosensitive Gas Generating Agent (C1)

After the interior of a reaction vessel is put in a nitrogen atmosphere, the following reagent and solvent were charged in the reaction vessel at room temperature. 2-Diazo-1,2-naphthoquinone-5-sulfonyl chloride: 46.2 parts Dichloromethane: 1 L Then, the reaction solution was cooled to 0° C.; 60 parts of triethylamine was added; and then, a dichloromethane solution of the reaction intermediate X2 was added dropwise. Then, the reaction solution was stirred at 0° C. for 1 hour, and was thereafter heated to room temperature, and stirred further for 2 hours at this temperature (room temperature). Then, 500 ml of water was added to the reaction solution; and thereafter, an organic layer was extracted with chloroform, and dried. Then, the organic layer was concentrated under reduced pressure to thereby obtain a crude product. Then, the crude product was purified with silica gel column chromatography, and thereafter dried at 40° C. under reduced pressure to thereby obtain a photosensitive gas generating agent (C1).

Here, the photosensitive gas generating agent (C1) obtained by the present Example is a compound represented by the general formula (2), and specific names of each substituent are as shown in the following Table 1. Here, in the photosensitive gas generating agent (C1) obtained by the present Example, n in the general formula (2) is 4.

TABLE 1

| Substituent | Specific Name |
| --- | --- |
| $R_{G2}$ | 2-diazo-1,2-naphthoquinone-5-sulfonyl group |
| $X_B$ | ethylene group |
| $R_1$ | ethylene group |
| $R_2$ | ethyl group |
| $R_f$ | 1H,1H,2H,2H-perfluorooctyl group |

Example 2

Production of a Photocurable Composition (a-1)

The following reagents were mixed.
(2-1) A polymerizable compound (A1): 94 parts by weight
  Here, as the polymerizable compound (A1), a mixture made by mixing the following reagents and solvent was used.
(2-1-1) Isobornyl acrylate (made by Kyoeisha Chemical Co., Ltd., trade name: IB-XA): 61.6 parts by weight
(2-1-2) (2-Methyl-2-ethyl-1,3-dioxolan-4-yl)methyl acrylate (made by Osaka Organic Chemical Industry Ltd., trade name: MEDOL-10): 10 parts by weight
(2-1-3) Hexandiol diacrylate (made by Osaka Organic Chemical Industry Ltd., trade name: Viscoat #230): 22.4 parts by weight
(2-2) A photopolymerization initiator (B1): 1 part by weight
  Here, as the photopolymerization initiator (B1), Irgacure 369 (made by Ciba Japan K.K.) was used.
(2-3) The photosensitive gas generating agent (C1) synthesized in Example 1: 12 parts by weight Then, the obtained mixed solution was filtered by a ultrahigh molecular weight polyethylene filter having a filter mesh of 5 nm to thereby obtain a photocurable composition (a-1).

[Evaluation of Photocurable Composition (a-1)]

A film was fabricated by the following method by using the obtained photocurable composition (a-1), and the photocurable composition (a-1) was then evaluated. A film was also fabricated, and the mold releasability provided by the photosensitive gas generating agent (C1) synthesized in Example 1 was also evaluated.

(Applying Step)

2 µl of the photocurable composition (a-1) was dropped on a silicon substrate (50 mm long, 25 mm wide) having an adhesion accelerating layer of 60 nm in thickness formed as an adhesion layer, by using a micro pipet.

(Mold Contact Step)

Then, a quartz substrate (50 mm long, 25 mm wide) having no surface treatment and no pattern formed thereon was placed on the silicon substrate so that the substrates cross each other at their centers; and the photocurable composition (a-1) was filled in the portion (25 mm long, 25 mm wide) where the silicon substrate and the quartz substrate were superposed. The film thickness of a liquid film of the photocurable composition (a-1) formed at this time was about 3.2 µm.

(Light Irradiation Step)

Then, the photocurable composition (a-1) was irradiated with UV light through the quartz substrate for 40 sec by using a UV light source (EX-250, made by HOYA CANDEO OPTRONICS Corp.) to thereby fabricate a film of a cured product of the photocurable composition (a-1).

(Mold Releasing Step)

Then, the silicon substrate and the quartz substrate were separated by hand.

In Example 2, such a situation could be observed during the light irradiation step that a gap was produced at the interface between the quartz substrate and the film of the photocurable composition along with the gas generation. If a gap is produced at the interface between the quartz substrate and the film of the photocurable composition in such a way, since the interfacial bonding force between the quartz substrate and the film naturally decreases, it can be considered that the effect of reducing the mold releasing force is attained. Here, the gap of the interface gradually vanished due to escape of the gas from the interface, and the gap completely vanished before the mold releasing step. In the mold releasing step, the silicon substrate and the quartz substrate could be remarkably easily separated.

Comparative Example 1

A photocurable composition (b-1) was prepared by the same method as in Example 2, except for using 2 parts by weight of 2-diazo-1,2-naphthoquinone-5-sulfonic acid p-cresol ester (PC-5, made by Toyo Gosei Co., Ltd.) in place of the photosensitive gas generating agent (C1) in Example 2. Then, a film was fabricated by the same method as in Example 2 by using the prepared photocurable composition (b-1), and the mold releasability of the photosensitive gas generating agent in the fabrication procedure of the film was evaluated.

In the present Comparative Example, the time (light exposure time) of light irradiation to the photocurable composition (b-1) in the light irradiation step was set for 40 sec, but such a situation could not be observed during the light irradiation that a gap was produced at the interface between the quartz substrate and the photocurable composition. Extension of the light exposure time from 40 sec to 600 sec also gave the same result. Further in the mold releasing step, since the silicon substrate and the quartz substrate strongly adhered to each other, they were difficult to separate by hand.

Comparative Example 2

A photocurable composition (b-2) was prepared by the same method as in Example 2, except for using 15 parts by weight of 2,2'-azobis-(N-butyl-2-methylpropionamide) (VAm-110, made by Wako Pure Chemical Industries, Ltd.) in place of the photosensitive gas generating agent (C1) in Example 2. Then, a film was fabricated by the same method as in Example 2 by using the prepared photocurable composition (b-2), and the mold releasability of the photosensitive gas generating agent in the fabrication procedure of the film was evaluated.

In the present Comparative Example, the time (light exposure time) of light irradiation to the photocurable composition (b-2) in the light irradiation step was at first set for 40 sec, but such a situation could not be observed during the light irradiation that a gap was produced at the interface between the quartz substrate and the photocurable composition. Then, the light exposure time was extended from 40 sec to 600 sec; then, such a situation was observed after 600 sec that a gap was produced at the interface between the quartz substrate and the photocurable composition along with the gas generation. Here, the gap of the interface gradually vanished due to escape of the gas from the interface, and the gap completely vanished before the mold releasing step carried out after the 600-sec light exposure. In the mold releasing step carried out after the 600-sec light exposure, the adhesion between the silicon substrate and the quartz substrate was not so strong as the adhesion in Comparative Example 1, but stronger than the adhesion in Example 2; therefore, a stronger force than the force in Example 2 was needed for mold releasing.

SUMMARY

From the above, it was clear that the photocurable composition of Example 2 having the photosensitive gas generating agent of Example 1 could be separated from the mold by a weaker force in the short light exposure time (40 sec) than the photocurable compositions of Comparative Examples. That is, it was revealed that a photocurable composition containing the photosensitive gas generating agent according to the present invention was a photocurable composition excellent in the effect of reducing the mold releasing force even in a small amount of light exposure. From comparison of Example 2 to Comparative Example 2, it is also clear that the photocurable composition according to the present invention exhibits the effect of suppressing re-adhesion of the silicon substrate with the quartz substrate even if the gas escapes from the interface between the film formed on the silicon substrate and the quartz substrate after mold releasing by the gas. This indicates that the use of the photocurable composition according to the present invention for nanoimprint lithography has an excellent effect of reducing the mold releasing force.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2013-043356, filed Mar. 5, 2013, and 2013-272409, filed Dec. 27, 2013, which are hereby incorporated by reference herein in their entirety.

REFERENCE SIGNS LIST 1 photocurable composition
2 substrate
3 mold
11 coating film
12 photocured product

The invention claimed is:

1. A photocurable composition, comprising:
   a polymerizable compound;
   a photopolymerization initiator; and
   a photosensitive gas generating agent, which is distributed unevenly at a gas-liquid interface of the photocurable composition,
   wherein the photosensitive gas generating agent is a compound having:
   a photostimulation responsive gas generating group to generate a gas by photostimulation;
   a perfluoroalkyl group; and
   a polyalkyleneoxy group to link the photostimulation responsive gas generating group and the perfluoroalkyl group.

2. The photocurable composition according to claim 1, wherein a content of the photosensitive gas generating agent is 1 wt % or more based on a weight of the polymerizable compound.

3. The photocurable composition according to claim 1, wherein the photocurable composition is suitable for use in nanoimprint lithography.

4. The photocurable composition according to claim 1, wherein a ratio of a weight of the photosensitive gas generating agent to a weight of the photopolymerization initiator is 1 to 1,000.

5. The photocurable composition according to claim 1, wherein the polymerizable compound is a radically polymerizable compound having at least one acryloyl group or methacryloyl group.

6. The photocurable composition according to claim 1, wherein the photosensitive gas generating agent is a compound of general formula (1):

$$R_{G1}-X_A-(O-R_1)_n-O-R_f \qquad (1),$$

wherein $R_{G1}$ is the photostimulation responsive gas generating group; $X_A$ is a divalent substituent to become a linking group; O is an oxygen atom; $R_1$ is an alkylene group having 2 to 4 carbon atoms; n is an integer of 2 to 30; and $R_f$ is a monovalent perfluoroalkyl group.

7. The photocurable composition according to claim 6, wherein $R_{G1}$ is a diazonaphthoquinonesulfonyl group.

8. A method for producing a film from the photocurable composition according to claim 1, the method comprising steps of:
   disposing the photocurable composition on a substrate;
   bringing the photocurable composition into contact with a mold;
   irradiating the photocurable composition with light;
   after the light irradiation, separating the photocurable composition and the mold, to thereby obtain the film having a predetermined pattern shape on the substrate.

9. A method for manufacturing a substrate with a circuit, comprising: carrying out etching or ion implantation based on a pattern shape of the film obtained by the method according to claim 8 to thereby form a circuit structure on the substrate based on the pattern shape.

10. An optical member, comprising:
a substrate; and
a film disposed on the substrate,
wherein the film is produced by the method according to claim 8.

11. The method according to claim 8, wherein the mold contact is carried out under an atmosphere containing a condensable gas.

12. The method according to claim 11, wherein the condensable gas is 1,1,1,3,3-pentafluoropropane.

13. The method according to claim 11, wherein the atmosphere is a mixed gas of helium and the condensable gas.

* * * * *